US012797122B2

(12) United States Patent
Altman et al.

(10) Patent No.: US 12,797,122 B2
(45) Date of Patent: Nov. 17, 2026

(54) FOLLOW WAVE PROPAGATION

(71) Applicant: BIOSENSE WEBSTER (ISRAEL) LTD., Yokneam (IL)

(72) Inventors: Sigal Altman, Ramat Hashofet (IL); Fady Massarwa, Baka Al Gharbiyua (IL); Gal Bar Zohar, Yokneam Moshara (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 636 days.

(21) Appl. No.: 17/344,194

(22) Filed: Jun. 10, 2021

(65) Prior Publication Data

US 2022/0395321 A1 Dec. 15, 2022

(51) Int. Cl.

| | |
|---|---|
| ***A61B 90/30*** | (2016.01) |
| ***A61B 18/14*** | (2006.01) |
| ***A61B 90/00*** | (2016.01) |
| *A61B 18/00* | (2006.01) |

(52) U.S. Cl.

CPC ........ *A61B 18/1492* (2013.01); *A61B 90/361* (2016.02); *A61B 90/37* (2016.02); *A61B 2018/00351* (2013.01)

(58) Field of Classification Search

CPC .............................. A61B 90/361; A61B 90/37
USPC .......................................................... 600/509
See application file for complete search history.

(56) References Cited

U.S. PATENT DOCUMENTS 5,391,199 A 2/1995 Ben Haim
5,687,737 A 11/1997 Branham
6,226,542 B1 5/2001 Reisfeld
6,239,724 B1 5/2001 Doron
6,301,496 B1 10/2001 Reisfeld
6,332,089 B1 12/2001 Acker
6,484,118 B1 11/2002 Govari
6,618,612 B1 9/2003 Acker
6,690,963 B2 2/2004 Ben Haim
6,892,091 B1 5/2005 Ben Haim
7,756,576 B2 7/2010 Levin
7,848,787 B2 12/2010 Osadchy
(Continued)

FOREIGN PATENT DOCUMENTS

EP 3476286 A1 5/2019
WO WO1996005768 A1 2/1996
WO WO-2019217430 A1 * 11/2019 ....... A61B 17/22004

OTHER PUBLICATIONS

European Search report for corresponding EPA No. 22177982.0 dated Nov. 9, 2022.

*Primary Examiner* — Allen Porter

(57) ABSTRACT

In one embodiment, a medical system includes a catheter configured to be inserted into a chamber of a heart, and including electrodes configured to capture electrical activity of tissue of the chamber over time, a display, and processing circuitry configured to compute a propagation of a cardiac activation wave over an anatomical map of the chamber of the heart from a start time in a cardiac cycle to an end time in the cardiac cycle responsively to the captured electrical activity, and render to the display respective portions of the propagation of the cardiac activation wave over respective portions of the anatomical map as viewed from a virtual camera while manipulating the virtual camera to follow progression of the propagation of the cardiac activation wave over the anatomical map.

14 Claims, 12 Drawing Sheets

(56) References Cited

U.S. PATENT DOCUMENTS

| | | | | |
|---|---|---|---|---|
| 7,869,865 | B2 | 1/2011 | Govari | |
| 10,136,828 | B2 | 11/2018 | Houben | |
| 10,918,310 | B2 | 2/2021 | Cohen | |
| 11,751,794 | B2 * | 9/2023 | Deno | A61B 5/367 600/509 |
| 12,064,252 | B2 * | 8/2024 | Hagfors | A61B 5/318 |
| 2002/0065455 | A1 | 5/2002 | Ben Haim | |
| 2003/0120150 | A1 | 6/2003 | Govari | |
| 2004/0068178 | A1 | 4/2004 | Govari | |
| 2004/0098175 | A1 * | 5/2004 | Said | G01C 21/3632 701/1 |
| 2007/0100332 | A1 | 5/2007 | Paul | |
| 2009/0093806 | A1 | 4/2009 | Govari et al. | |
| 2009/0138007 | A1 | 5/2009 | Govari | |
| 2009/0262980 | A1 * | 10/2009 | Markowitz | G06V 20/64 382/128 |
| 2014/0278324 | A1 | 9/2014 | Bates | |
| 2015/0348310 | A1 | 12/2015 | Watanabe et al. | |
| 2017/0202469 | A1 | 7/2017 | Scharf | |
| 2017/0281031 | A1 * | 10/2017 | Houben | A61B 18/1492 |
| 2018/0078146 | A1 * | 3/2018 | Shadforth | A61B 5/015 |
| 2018/0182157 | A1 * | 6/2018 | Zar | G06T 15/04 |
| 2019/0183576 | A1 * | 6/2019 | Fahim | A61B 90/36 |
| 2019/0336023 | A1 | 11/2019 | Lou | |
| 2020/0113465 | A1 | 4/2020 | Cohen et al. | |
| 2020/0375555 | A1 * | 12/2020 | Cohen | A61B 5/339 |
| 2021/0068694 | A1 | 3/2021 | Chou et al. | |
| 2021/0106243 | A1 * | 4/2021 | Altmann | A61B 5/7425 |
| 2021/0169394 | A1 * | 6/2021 | Chou | A61B 34/10 |
| 2021/0228147 | A1 * | 7/2021 | Wang | A61B 5/296 |
| 2022/0079462 | A1 * | 3/2022 | Massarwi | A61B 5/055 |
| 2022/0202338 | A1 * | 6/2022 | Zhu | A61B 5/35 |
| 2022/0346867 | A1 * | 11/2022 | Harlev | A61B 5/367 |
| 2023/0073299 | A1 * | 3/2023 | Afonso | A61B 5/339 |

* cited by examiner

FOLLOW WAVE PROPAGATION

FIELD OF THE INVENTION

The present invention relates to medical systems, and in particular, but not exclusively to, catheter-based systems.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178, whose disclosures are all incorporated herein by reference. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied to the tip electrode(s) of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue.

Heating of the tissue occurs due to its electrical resistance. The tissue is heated sufficiently to cause cellular destruction in the cardiac tissue resulting in formation of a lesion within the cardiac tissue which is electrically non-conductive.

Therefore, when placing an ablation or other catheter within the body, particularly near the endocardial tissue, it is desirable to have the distal tip of the catheter in direct contact with the tissue. The contact can be verified, for example, by measuring the contact between the distal tip and the body tissue. U.S. Patent Application Publication Nos. 2007/0100332, 2009/0093806 and 2009/0138007, describe methods of sensing contact pressure between the distal tip of a catheter and tissue in a body cavity using a force sensor embedded in the catheter.

SUMMARY

There is provided in accordance with an embodiment of the present disclosure, a medical system, including a catheter configured to be inserted into a chamber of a heart, and including electrodes configured to capture electrical activity of tissue of the chamber over time, a display, and processing circuitry configured to compute a propagation of a cardiac activation wave over an anatomical map of the chamber of the heart from a start time in a cardiac cycle to an end time in the cardiac cycle responsively to the captured electrical activity, and render to the display respective portions of the propagation of the cardiac activation wave over respective portions of the anatomical map as viewed from a virtual camera while manipulating the virtual camera to follow progression of the propagation of the cardiac activation wave over the anatomical map.

Further in accordance with an embodiment of the present disclosure the virtual camera is disposed inside the anatomical map, and the processing circuitry is configured to render to the display the respective portions of the propagation of the cardiac activation wave over the respective portions of the anatomical map as viewed from the virtual camera inside the anatomical map while manipulating the virtual camera to follow progression of the propagation of the cardiac activation wave over the inside of the anatomical map.

Still further in accordance with an embodiment of the present disclosure the processing circuitry is configured to find local activation times at corresponding positions on the anatomical map responsively to the captured electrical activity, and render to the display the respective portions of the propagation of the cardiac activation wave over the respective portions of the anatomical map as viewed from a virtual camera while manipulating the virtual camera to follow progression of the propagation of the cardiac activation wave over the anatomical map responsively to respective ones of the local activation times at respective ones of the corresponding positions.

Additionally, in accordance with an embodiment of the present disclosure the processing circuitry is configured to define a local activation time (LAT) window, move the LAT window through a time period in the cardiac cycle over respective ranges of the local activation times in the time period, and render to the display the respective portions of the propagation of the cardiac activation wave over the respective portions of the anatomical map responsively to the respective ranges of the local activation times in the LAT window moving through the time period.

Moreover, in accordance with an embodiment of the present disclosure the processing circuitry is configured to manipulate the virtual camera to follow the progression of the propagation of the cardiac activation wave over the anatomical map responsively to the LAT window moving through the time period.

Further in accordance with an embodiment of the present disclosure the processing circuitry is configured to find a path for the virtual camera to follow, and manipulate the virtual camera to follow the progression of the propagation of the cardiac activation wave responsively to the found path.

Still further in accordance with an embodiment of the present disclosure the processing circuitry is configured to find local activation times at corresponding positions on the anatomical map responsively to the captured electrical activity, and render to the display the respective portions of the propagation of the cardiac activation wave over the respective portions of the anatomical map as viewed from the virtual camera while manipulating the virtual camera to follow the progression of the propagation of the cardiac activation wave over the anatomical map responsively to the found path and respective ones of the local activation times at respective ones of the corresponding positions along the found path.

Additionally, in accordance with an embodiment of the present disclosure the processing circuitry is configured to adjust a field of view of the virtual camera a size of the cardiac activation wave along the found path.

Moreover, in accordance with an embodiment of the present disclosure the processing circuitry is configured to receive user input, which designs the path.

Further in accordance with an embodiment of the present disclosure the processing circuitry is configured to find a plurality of paths for the virtual camera to follow.

Still further in accordance with an embodiment of the present disclosure the processing circuitry is configured to select a longest one of the paths, and manipulate the virtual camera to follow the progression of the propagation of the cardiac activation wave responsively to the longest one of the paths.

Additionally, in accordance with an embodiment of the present disclosure the processing circuitry is configured to receive user input selecting one of the paths for the virtual camera to follow.

There is also provided in accordance with another embodiment of the present disclosure, a medical method, including computing a propagation of a cardiac activation wave over an anatomical map of the chamber of the heart from a start time in a cardiac cycle to an end time in the cardiac cycle responsively to electrical activity of tissue of a chamber of a heart captured over time by electrodes of a catheter inserted into the chamber, and rendering to a display respective portions of the propagation of the cardiac activation wave over respective portions of the anatomical map as viewed from a virtual camera while manipulating the virtual camera to follow progression of the propagation of the cardiac activation wave over the anatomical map.

Moreover in accordance with an embodiment of the present disclosure the virtual camera is disposed inside the anatomical map, and the rendering includes rendering to the display the respective portions of the propagation of the cardiac activation wave over the respective portions of the anatomical map as viewed from the virtual camera inside the anatomical map while manipulating the virtual camera to follow progression of the propagation of the cardiac activation wave over the inside of the anatomical map.

Further in accordance with an embodiment of the present disclosure, the method includes finding local activation times at corresponding positions on the anatomical map responsively to the captured electrical activity, and wherein the rendering includes rendering to the display the respective portions of the propagation of the cardiac activation wave over the respective portions of the anatomical map as viewed from a virtual camera while manipulating the virtual camera to follow progression of the propagation of the cardiac activation wave over the anatomical map responsively to respective ones of the local activation times at respective ones of the corresponding positions.

Still further in accordance with an embodiment of the present disclosure, the method includes defining a local activation time (LAT) window, and moving the LAT window through a time period in the cardiac cycle over respective ranges of the local activation times in the time period, and wherein the rendering includes rendering to the display the respective portions of the propagation of the cardiac activation wave over the respective portions of the anatomical map responsively to the respective ranges of the local activation times in the LAT window moving through the time period.

Additionally, in accordance with an embodiment of the present disclosure the manipulating includes manipulating the virtual camera to follow the progression of the propagation of the cardiac activation wave over the anatomical map responsively to the LAT window moving through the time period.

Moreover, in accordance with an embodiment of the present disclosure, the method includes finding a path for the virtual camera to follow, and wherein the manipulating includes manipulating the virtual camera to follow the progression of the propagation of the cardiac activation wave responsively to the found path.

Further in accordance with an embodiment of the present disclosure the finding includes finding local activation times at corresponding positions on the anatomical map responsively to the captured electrical activity, and the rendering includes rendering to the display the respective portions of the propagation of the cardiac activation wave over the respective portions of the anatomical map as viewed from the virtual camera while manipulating the virtual camera to follow the progression of the propagation of the cardiac activation wave over the anatomical map responsively to the found path and respective ones of the local activation times at respective ones of the corresponding positions along the found path.

Still further in accordance with an embodiment of the present disclosure, the method includes adjusting a field of view of the virtual camera a size of the cardiac activation wave along the found path.

Additionally, in accordance with an embodiment of the present disclosure, the method includes receiving user input, which designs the path.

Moreover, in accordance with an embodiment of the present disclosure, the method includes finding a plurality of paths for the virtual camera to follow.

Further in accordance with an embodiment of the present disclosure, the method includes selecting a longest one of the paths, and wherein the manipulating includes manipulating the virtual camera to follow the progression of the propagation of the cardiac activation wave responsively to the longest one of the paths.

Still further in accordance with an embodiment of the present disclosure, the method includes receiving user input selecting one of the paths for the virtual camera to follow.

There is also provided in accordance with still another embodiment of the present disclosure, a software product, including a non-transient computer-readable medium in which program instructions are stored, which instructions, when read by a central processing unit (CPU), cause the CPU to compute a propagation of a cardiac activation wave over an anatomical map of the chamber of the heart from a start time in a cardiac cycle to an end time in the cardiac cycle responsively to electrical activity of tissue of a chamber of a heart captured over time by electrodes of a catheter inserted into the chamber, and render to a display respective portions of the propagation of the cardiac activation wave over respective portions of the anatomical map as viewed from a virtual camera while manipulating the virtual camera to follow progression of the propagation of the cardiac activation wave over the anatomical map.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
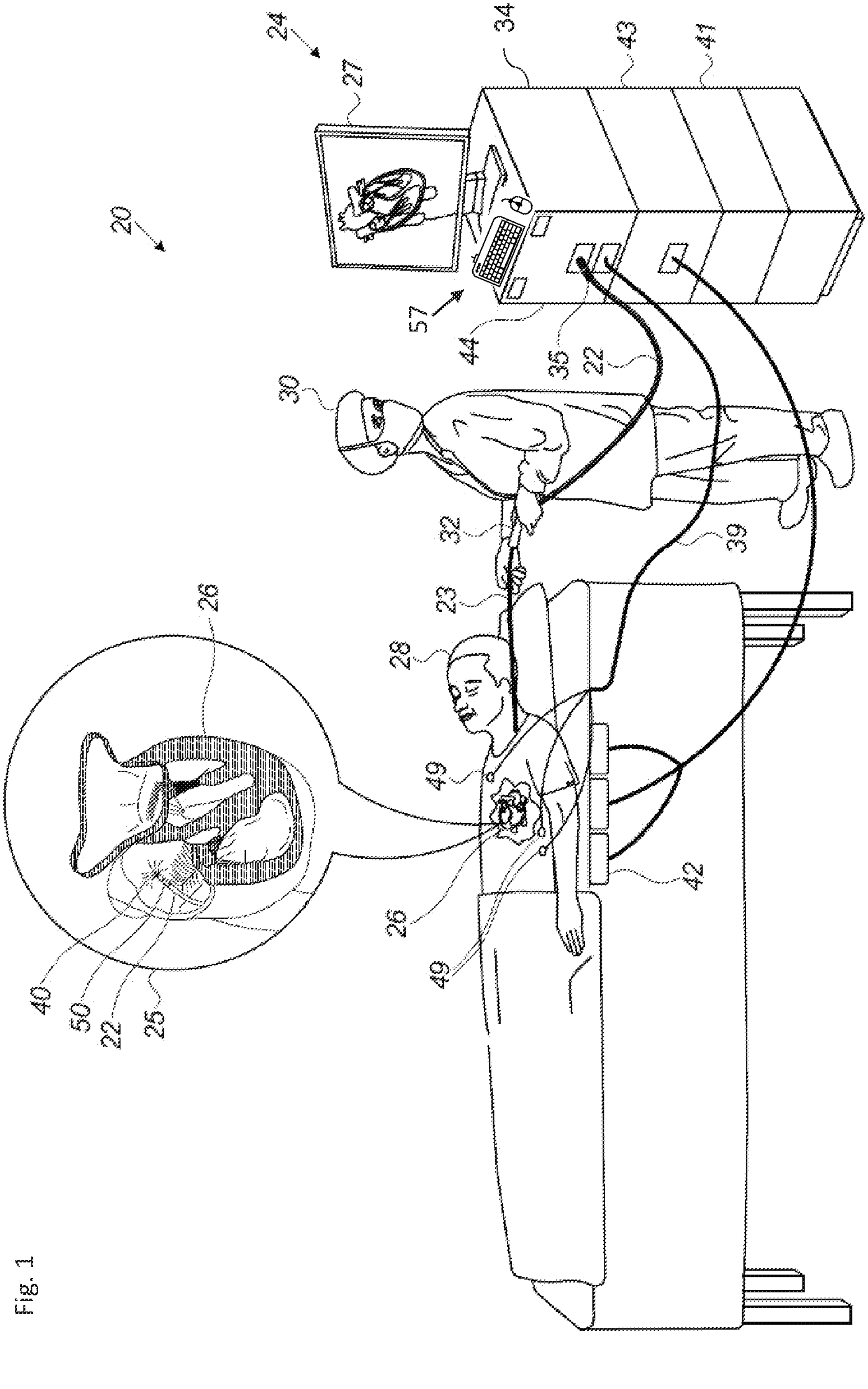
FIG. 1 is a schematic view of a medical procedure system constructed and operative in accordance with an exemplary embodiment of the present invention.

As mentioned previously, in a two-step procedure, mapping followed by ablation, electrical activity at points within the heart is typically sensed and measured by advancing a catheter containing one or more electrodes into the heart, and acquiring data at a multiplicity of points. These data are then utilized to select the target areas at which the ablation is to be performed.

The mapping may be used to compute a propagation of a cardiac activation wave over a chamber of the heart from a start time in a cardiac cycle to an end time in the cardiac cycle responsively to captured electrical activity, such as local activation times (LATs). The propagation of the cardiac activation wave may be rendered to a display, typically in slow motion (or at any suitable selected speed), over an anatomical map of the chamber using colors and/or symbols. The propagation is then analyzed via a physician to determine if and where to ablate the tissue of the chamber of the heart.

The physician may be viewing a sub-region of the anatomical map, for example, the physician may want to zoom into a sub-region of the anatomical map or view a sub-region of the anatomical map from inside the anatomical map (e.g., from the viewpoint of a virtual camera in which only the sub-region of the map can be viewed at any one time). Assuming that the selected sub-region of the anatomical map is not at the start of the wave propagation, and the physician then runs the propagation of the cardiac activation wave over the anatomical map of the chamber of the heart, the physician will not see the propagation on the selected rendered sub-region of the anatomical map until after some delay, i.e., until the wave finally reaches the selected rendered sub-region of the anatomical map after "running" over the non-rendered portions of the map. If the wave propagation is run in a loop mode whereby the wave propagation runs from beginning to end and then repeats from the beginning etc., the delay may be even greater as the physician needs to wait while the wave propagation is running over the non-rendered portions of the anatomical map prior to, and after, the selected rendered sub-regions of the map currently being viewed. Once the wave propagation enters the selected rendered sub-region, the wave propagation disappears quickly until the next repeat of the wave propagation after another delay. The delay in the wave being visible in the selected sub-region of the anatomical map may be confusing to the physician and wastes valuable time during a cardiac procedure especially when the physician needs to repeatedly run the wave propagation in order to determine if and where to ablate the tissue of the chamber of the heart based on the wave propagation.

Embodiments of the present invention solve the above problems by providing a system which renders to a display respective portions of a propagation of a cardiac activation wave over respective portions of a corresponding anatomical map as viewed from a virtual camera while manipulating the virtual camera to follow progression of the propagation of the cardiac activation wave over the anatomical map. In other words, the virtual camera may be moved automatically to follow the wave propagation as it moves over the surface of the anatomical map so that the portion of the map being rendered is the same portion over which the wave is currently propagating. For example, the positions (including orientations) of the virtual camera may be computed to follow the wave propagation as it moves over the surface of the map.

The system may compute a path for the virtual camera to follow. The virtual camera may then follow the path during the rendering of the wave propagation. In some embodiments, the virtual camera may be moved at a constant rate from the beginning of the path until the end of the path, commencing movement along the path with the start of the wave propagation. In some embodiments, the virtual camera may be moved at the speed of movement of the wave propagation, i.e., sometime slower and sometimes faster. In some embodiments, the virtual camera may be moved according to the center or a leading edge of the cardiac activation wave currently being rendered. In some embodiments, the field of view of the virtual camera may be adjusted over the path according to the size of the wave currently being rendered.

The system may compute multiple paths, for example, where the wave propagation splits or where the whole wave cannot be captured by the field of view of the virtual camera. The system may then select one of the paths, e.g., a longest one of the paths, for the virtual camera to follow. In some embodiments, a user may select which of the paths should be followed by the virtual camera. In some embodiments, the user may design the path to be followed on the anatomical map, for example, using a pointing device (e.g., mouse or stylus) or a touch-sensitive screen.

System Description

Figure 2:
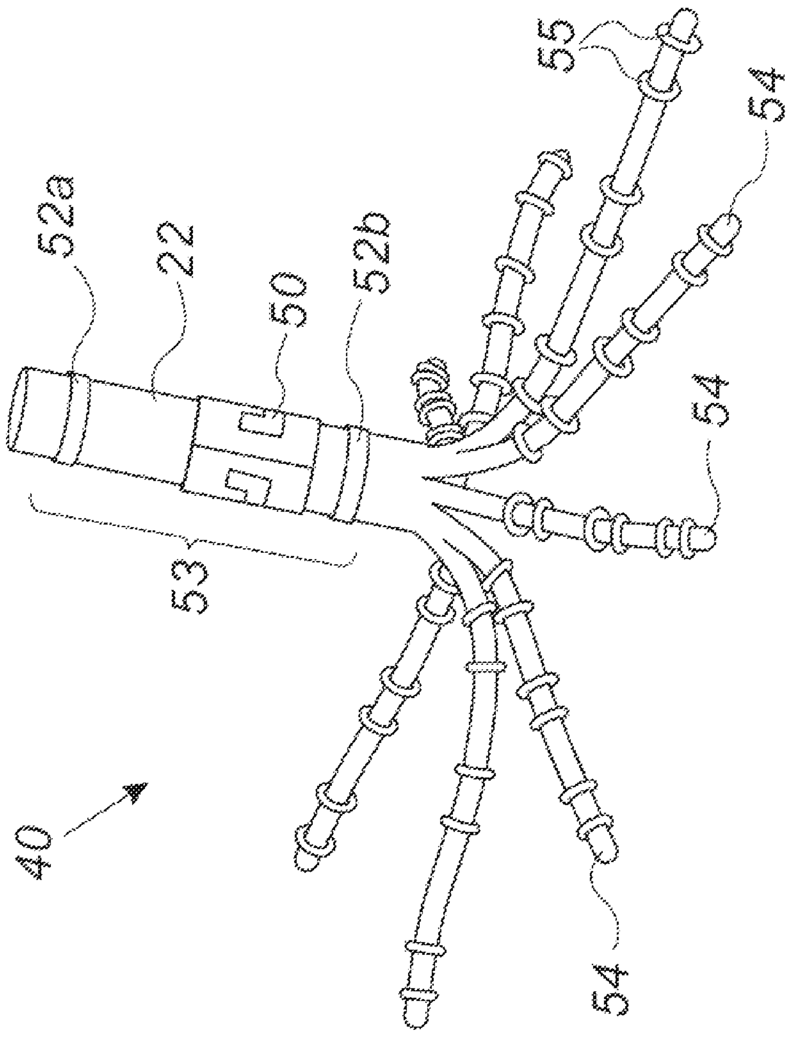
FIG. 2 is a schematic view of a catheter for use in the system of FIG. 1.

Reference is now made to FIG. 1, which is a schematic view of a medical procedure system 20 constructed and operative in accordance with an exemplary embodiment of the present invention. Reference is also made to FIG. 2, which is a schematic view of a catheter 40 for use in the system 20 of FIG. 1.

The medical procedure system 20 is used to determine the position of the catheter 40, seen in an inset 25 of FIG. 1 and in more detail in FIG. 2. The catheter 40 includes a shaft 22 and a plurality of flexible arms 54 (only some labeled for the sake of simplicity) having respective proximal ends connected to a distal end of the shaft 22. The catheter 40 is configured to be inserted into a body-part (e.g., a chamber of a heart 26) of a living subject.

The catheter 40 includes a position sensor 53 disposed on the shaft 22 in a predefined spatial relation to the proximal ends of the flexible arms 54. The position sensor 53 may include a magnetic sensor 50 and/or at least one shaft electrode 52. The magnetic sensor 50 may include at least one coil, for example, but not limited to, a dual-axis or a triple axis coil arrangement to provide position data for location and orientation including roll. The catheter 40 includes multiple electrodes 55 (only some are labeled in FIG. 2 for the sake of simplicity) disposed at respective locations along each of the flexible arms 54 and configured to capture electrical activity of tissue of a chamber of the heart 26 at respective positions in the heart 26 over time. Typically, the catheter 40 may be used for mapping electrical activity in the heart 26 of the living subject using the electrodes 55, or for performing any other suitable function in a body-part of a living subject.

The medical procedure system 20 may determine a position and orientation of the shaft 22 of the catheter 40 based on signals provided by the magnetic sensor 50 and/or the shaft electrodes 52 (proximal-electrode 52*a* and distal-electrode 52*b*) fitted on the shaft 22, on either side of the magnetic sensor 50. The proximal-electrode 52*a*, the distal-electrode 52*b*, the magnetic sensor 50 and at least some of the electrodes 55 are connected by wires running through the shaft 22 via a catheter connector 35 to various driver circuitries in a console 24. In some embodiments, at least two of the electrodes 55 of each of the flexible arms 54, the shaft electrodes 52, and the magnetic sensor 50 are connected to the driver circuitries in the console 24 via the catheter connector 35. In some embodiments, the distal electrode 52*b* and/or the proximal electrode 52*a* may be omitted.

The illustration shown in FIG. 2 is chosen purely for the sake of conceptual clarity. Other configurations of shaft electrodes 52 and electrodes 55 are possible. Additional functionalities may be included in the position sensor 53. Elements which are not relevant to the disclosed embodiments of the invention, such as irrigation ports, are omitted for the sake of clarity.

A physician 30 navigates the catheter 40 to a target location in a body part (e.g., heart 26) of a patient 28 by manipulating the shaft 22 using a manipulator 32 near the proximal end of the catheter 40 and/or deflection from a sheath 23. The catheter 40 is inserted through the sheath 23, with the flexible arms 54 gathered together, and only after the catheter 40 is retracted from the sheath 23, the flexible arms 54 are able to spread and regain their intended functional shape. By containing flexible arms 54 together, the sheath 23 also serves to minimize vascular trauma on its way to the target location.

Console 24 comprises processing circuitry 41, typically a general-purpose computer and a suitable front end and interface circuits 44 for generating signals in, and/or receiving signals from, body surface electrodes 49 which are attached by wires running through a cable 39 to the chest and to the back, or any other suitable skin surface, of the patient 28.

Console 24 further comprises a magnetic-sensing subsystem. The patient 28 is placed in a magnetic field generated by a pad containing at least one magnetic field radiator 42, which is driven by a unit 43 disposed in the console 24. The magnetic field radiator(s) 42 is configured to transmit alternating magnetic fields into a region where the body-part (e.g., the heart 26) is located. The magnetic fields generated by the magnetic field radiator(s) 42 generate direction signals in the magnetic sensor 50. The magnetic sensor 50 is configured to detect at least part of the transmitted alternating magnetic fields and provide the direction signals as corresponding electrical inputs to the processing circuitry 41.

In some embodiments, the processing circuitry 41 uses the position-signals received from the shaft electrodes 52, the magnetic sensor 50 and the electrodes 55 to estimate a position of the catheter 40 inside an organ, such as inside a cardiac chamber. In some embodiments, the processing circuitry 41 correlates the position signals received from the electrodes 52, 55 with previously acquired magnetic location-calibrated position signals, to estimate the position of the catheter 40 inside a cardiac chamber. The position coordinates of the shaft electrodes 52 and the electrodes 55 may be determined by the processing circuitry 41 based on, among other inputs, measured impedances, or on proportions of currents distribution, between the electrodes 52, 55 and the body surface electrodes 49. The console 24 drives a display 27, which shows the distal end of the catheter 40 inside an anatomical map of the heart 26.

The method of position sensing using current distribution measurements and/or external magnetic fields is implemented in various medical applications, for example, in the Carto® system, produced by Biosense Webster Inc. (Irvine, California), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publication Nos. 2002/0065455 A1, 2003/0120150 A1 and 2004/0068178 A1.

The Carto® 3 system applies an Active Current Location (ACL) impedance-based position-tracking method. In some embodiments, using the ACL method, the processing circuitry 41 is configured to create a mapping (e.g., current-position matrix (CPM)) between indications of electrical impedance and positions in a magnetic coordinate frame of the magnetic field radiator(s) 42. The processing circuitry 41 estimates the positions of the shaft electrodes 52 and the electrodes 55 by performing a lookup in the CPM.

Processing circuitry 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The system 20 also includes a user interface 57 to receive user input such as a selection of a sub-region of the anatomical map for display, manipulation of a virtual camera used in viewing the sub-region of the anatomical map, a rendering speed of a wave propagation of a cardiac activation wave, and/or a width of a cardiac activation wave being rendered. The user interface 57 may include a keyboard and/or touch screen, a foot pedal, and optionally a pointing device such as a mouse, stylus and/or joystick.

FIG. 1 shows only elements related to the disclosed techniques, for the sake of simplicity and clarity. The system 20 typically comprises additional modules and elements that are not directly related to the disclosed techniques, and thus are intentionally omitted from FIG. 1 and from the corresponding description.

The catheter 40 described above includes eight flexible arms 54 with six electrodes 55 per arm 54. Any suitable catheter may be used instead of the catheter 40, for example, a catheter with a different number of flexible arms and/or electrodes per arm, or a different probe shape such as a balloon catheter or a lasso catheter, by way of example only.

The medical procedure system 20 may also perform ablation of heart tissue using any suitable catheter, for example using the catheter 40 or a different catheter and any suitable ablation method. The console 24 may include an RF signal generator 34 configured to generate RF power to be applied by an electrode or electrodes of a catheter connected to the console 24, and one or more of the body surface electrodes 49, to ablate a myocardium of the heart 26. The console 24 may include a pump (not shown), which pumps irrigation fluid into an irrigation channel to a distal end of a catheter performing ablation. The catheter performing the ablation may also include temperature sensors (not shown) which are used to measure a temperature of the myocardium during ablation and regulate an ablation power and/or an irrigation rate of the pumping of the irrigation fluid according to the measured temperature.

Figure 3:
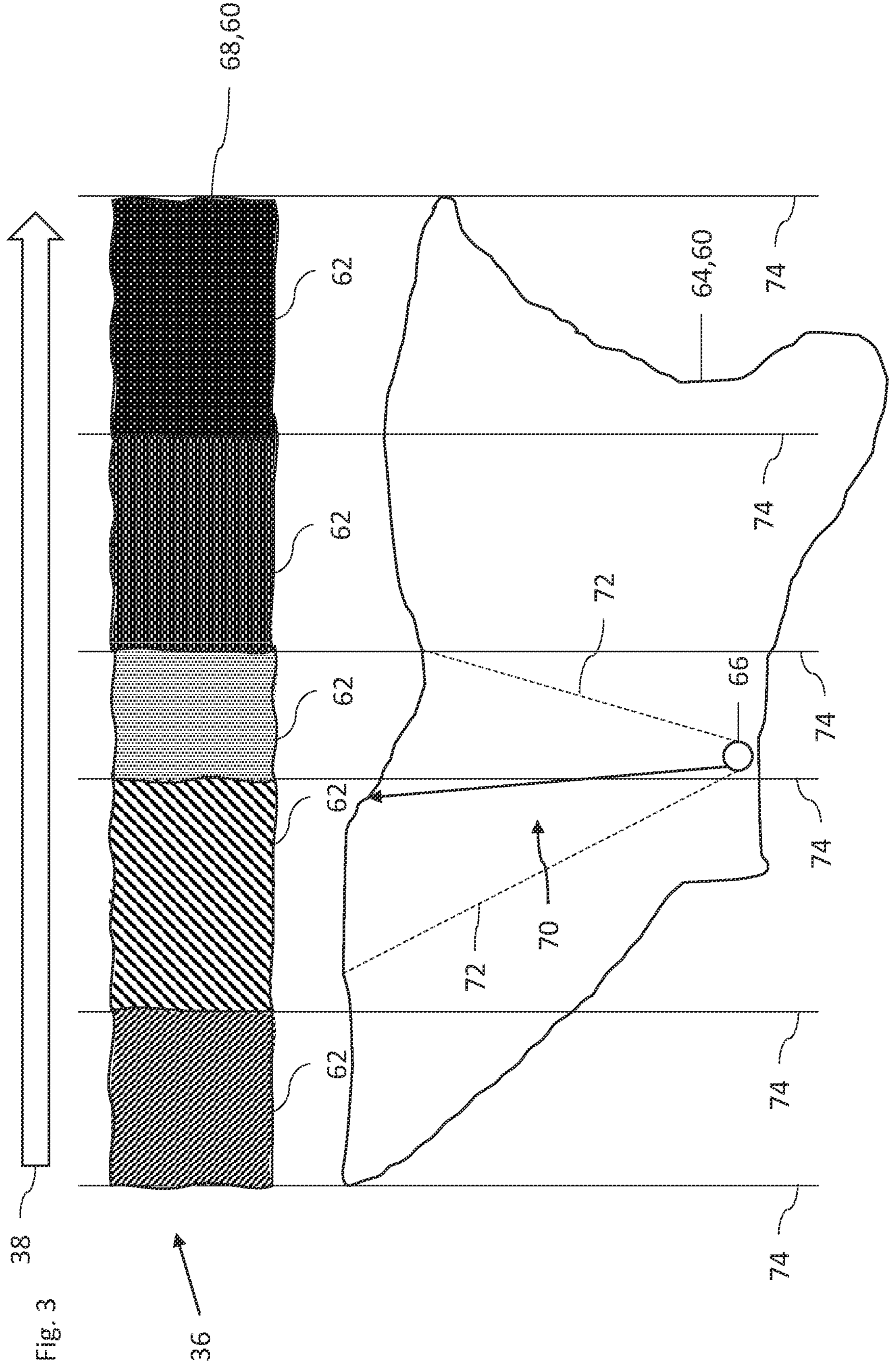
FIG. 3 is a schematic view of a local activation time map and propagation of a cardiac activation wave for use in the system of FIG. 1.

Reference is now made to FIG. 3, which is a schematic view of a local activation time map 36 and propagation of a cardiac activation wave for use in the system 20 of FIG. 1.

The processing circuitry 41 may be configured to generate an anatomical map 60 using any suitable anatomical map generation method, for example, but not limited to, Fast Anatomical Mapping (FAM). FAM is described in U.S. Pat. No. 10,918,310 to Cohen, et al. In FAM, a smooth shell is generated around a three-dimensional (3D) cloud of data points, such as a cloud of computed electrode positions of the electrodes 55.

The processing circuitry 41 is configured to find local activation times (LATs) at corresponding positions on the anatomical map 60 responsively to the electrical activity captured by the electrodes 55 of the catheter 40 over time. In some embodiments, the local activations times (LATs) are identified from the cardiac electrical activity signals (e.g., electrocardiograms (ECGs) or intracardiac electrograms (IEGMs)) and associated with respective positions on the surface of the anatomical map 60. The LATs may be represented on the local activation time map 36 by using different colors or shading to indicate different LAT ranges 62 or LAT values. For example, LATs in a range of −200 milliseconds (ms) to −190 ms may be represented by one color, and LATs within a range of −190 milliseconds (ms) to −180 ms may be represented by another color, and so on. Alternatively, each LAT value may correspond to a different color (e.g., −200 ms may be represented by blue, whereas −199 ms may be represented by a slightly different blue, and so on). For example, the LAT values in the range −200 ms to +200 ms may be represented by a color in the range of RGB values (0,0,255) to (255,0,0) with (255,255,0) in the middle of the range, respectively.

The processing circuitry 41 is configured to compute a propagation of a cardiac activation wave (having a direction indicated by arrow 38) over the anatomical map 60 of a chamber of the heart 26 from a start time in a cardiac cycle to an end time in the cardiac cycle responsively to electrical activity captured by the electrodes 55 of the catheter 40 over time. The propagation of the cardiac activation wave may be computed using any suitable method, for example, but not limited to, one or more of the methods disclosed in U.S. Pat. Nos. 10,136,828, 6,226,542, 6,301,496, and in 6,892,091. The propagation of the cardiac activation wave may be computed based on the LAT values using a sliding window of LATs. For example, at time T0 LATs in a range of −200 ms to −160 ms are rendered on the anatomical map 60, at time T1 LATs in a range −180 ms to −140 ms are rendered on the anatomical map 60, and at a time T2 LATs in a range −160 ms to −120 ms are rendered on the anatomical map 60, and so on. The LAT window continues to move until a complete cycle of the cardiac activation wave has been rendered over the anatomical map 60. In this way, the cardiac activation wave is seen to move over the surface of the anatomical map 60. The width of the sliding window, i.e., the range of LATs in the sliding window may be configurable. Color or shading may be used to indicate the LATs being rendered at any one time in the propagation. Different colors or shading may be used to indicate different LAT values. For example, LATs in the range of −200 ms to −160 ms may be rendered on the anatomical map 60 in red, LATs in the range −180 ms to −140 ms may be rendered on the anatomical map 60 in orange, LATs in a range −160 ms to −120 ms may be rendered on the anatomical map 60 in yellow, and so on. Alternatively, each LAT value may correspond to a different color (e.g., −200 ms may be represented by blue, whereas-199 ms may be represented by a slightly different blue, and so on). For example, the LAT values in the range −200 ms to +200 ms may be represented by a color in the range of RGB values (0,0,255) to (255,0,0) with (255,255,0) in the middle of the range, respectively.

FIG. 3 shows a cross-section 64 of the anatomical map 60 with a virtual camera 66 therein, with the virtual camera 66 facing an interior wall 68 of the anatomical map 60. The interior wall 68 is also shown above the cross-section 64 in FIG. 3. Vertical lines 74 are drawn across the interior wall 68 and the cross-section 64 of the anatomical map 60 to indicate the correspondence between the LAT ranges 62 shown on the interior wall 68 and where the LAT ranges are on the cross-section 64.

FIG. 3 shows that a field of view 70 (bounded by two dotted lines 72) of the virtual camera 66 is restricted to a portion of the local activation time map 36. Therefore, when the propagation of the cardiac activation wave is rendered to the display 27 based on a static position (including orientation) of the virtual camera 66, only a portion of the propagation will be seen on the display 27 and with a delay after running the propagation.

Reference is now made to FIGS. 4A-E, which are schematic views of propagation of a cardiac activation wave, and the virtual camera 66 for use in the system 20 of FIG. 1.

Figure 4A:
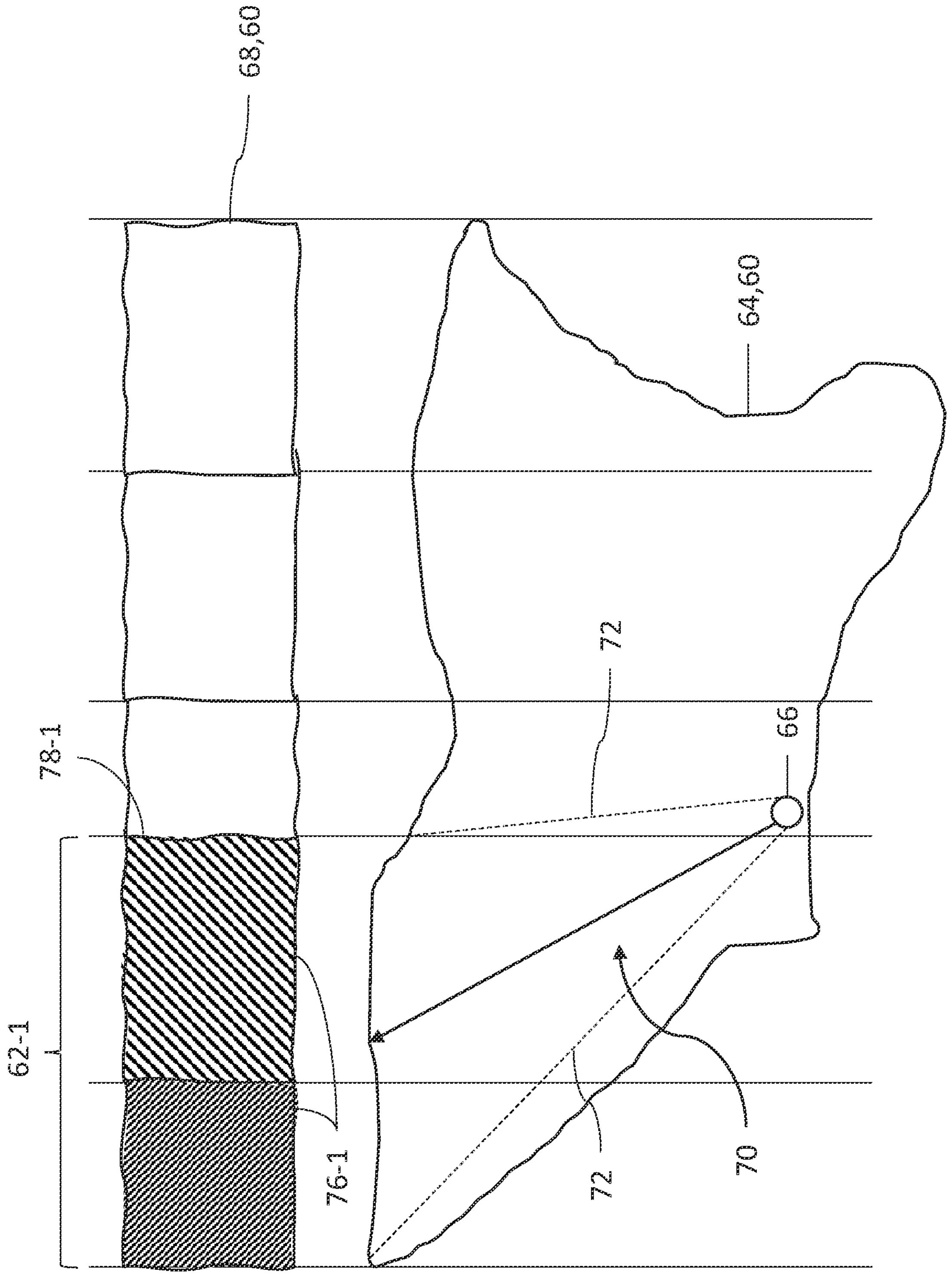
FIGS. 4A-E are schematic views of propagation of a cardiac activation wave and a virtual camera for use in the system of FIG. 1.

FIG. 4A shows two shaded regions 76-1 corresponding to a LAT range 62-1 of the local activation time map 36 (FIG. 3). The shaded regions 76-1 are rendered as part of the propagation of the cardiac activation wave corresponding to a time window including LAT range 62-1. Virtual camera 66 is shown in the cross-section 64 of the anatomical map 60 positioned (i.e., orientated) with the field of view 70 (dotted lines 72) of the virtual camera 66 facing towards the center of the shaded regions 76-1. The shaded regions 76-1 are therefore rendered to the display 27 with a corresponding portion 78-1 of the interior wall 68 of the anatomical map 60.

As the cardiac activation wave progresses along the interior wall 68 of anatomical map 60, corresponding to moving the time window of the LAT ranges 62 forward in time, the position of the virtual camera 66 is manipulated (e.g., turned clockwise) so that the field of view 70 of the virtual camera 66 is directed towards the center of the progressing cardiac activation wave.

Figure 4B:
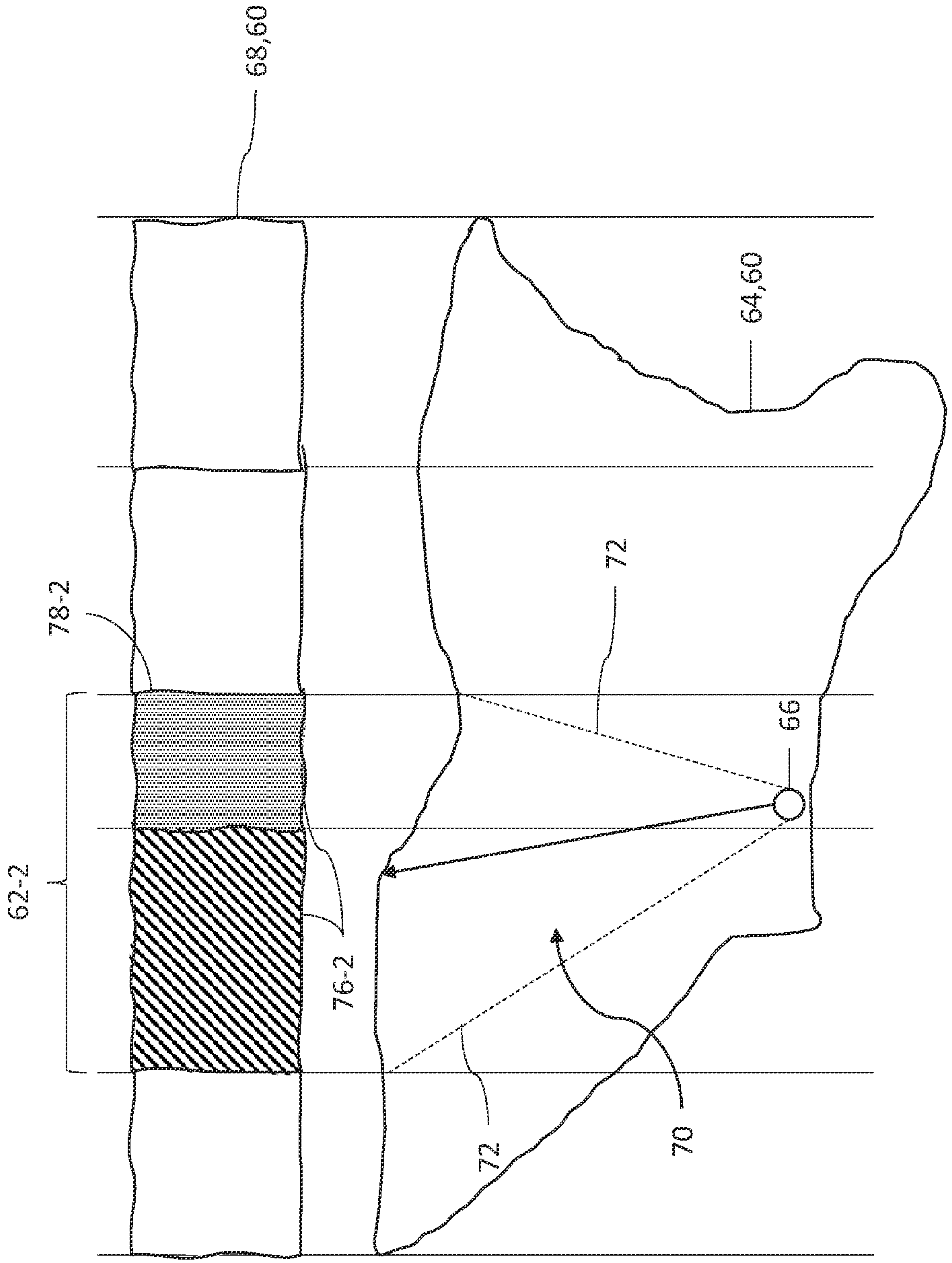

FIG. 4B shows two shaded regions 76-2 corresponding to a LAT range 62-2 of the local activation time map 36 (FIG. 3). The shaded regions 76-2 are rendered as part of the propagation of the cardiac activation wave corresponding to a time window including LAT range 62-2. Virtual camera 66 is shown in the cross-section 64 of the anatomical map 60 positioned (i.e., orientated) with the field of view 70 (dotted lines 72) of the virtual camera 66 facing towards the center of the shaded regions 76-2. The shaded regions 76-2 are therefore rendered to the display 27 with a corresponding portion 78-2 of the interior wall 68 of the anatomical map 60.

Figure 4C:
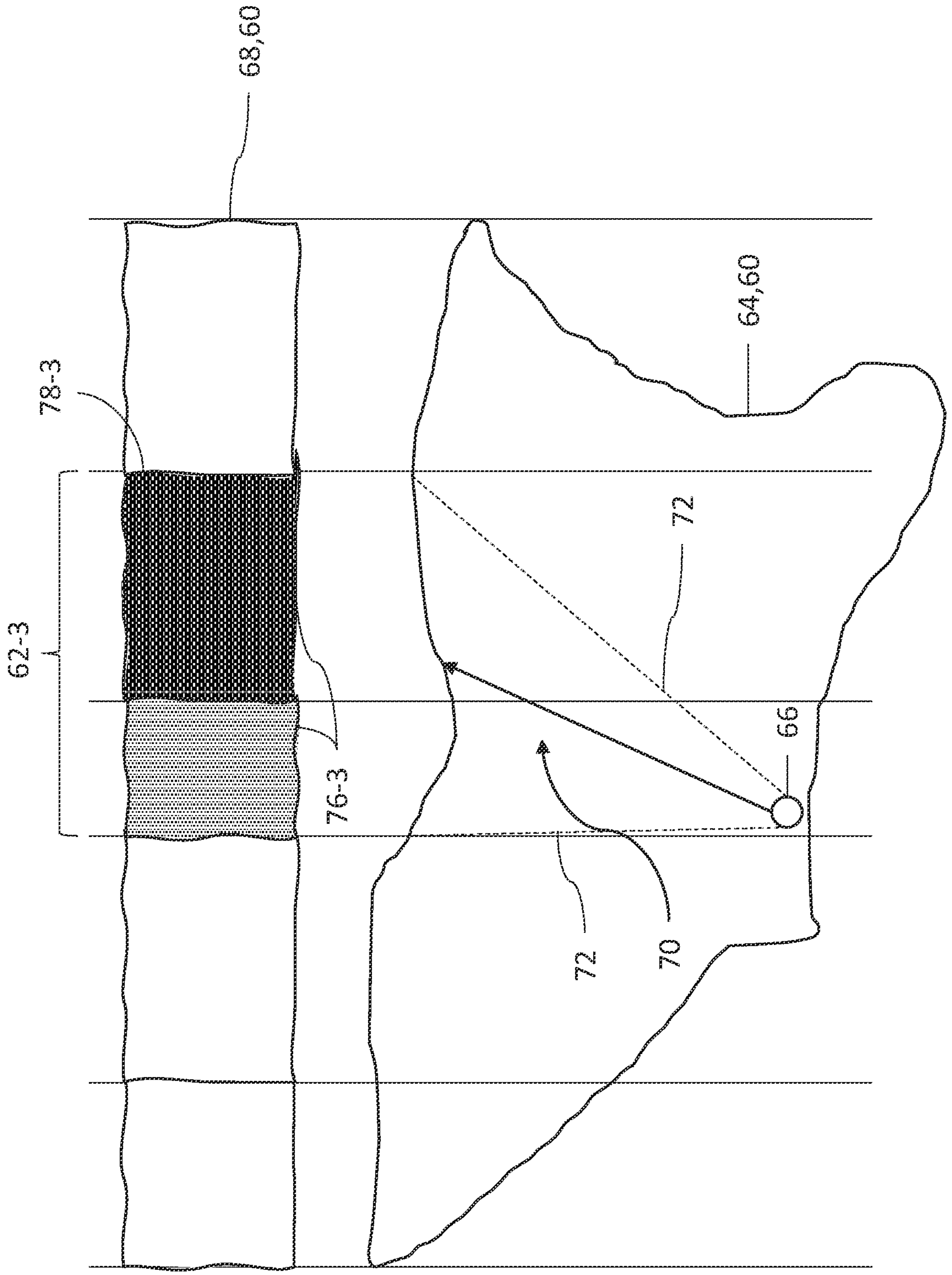
Figure 4D:
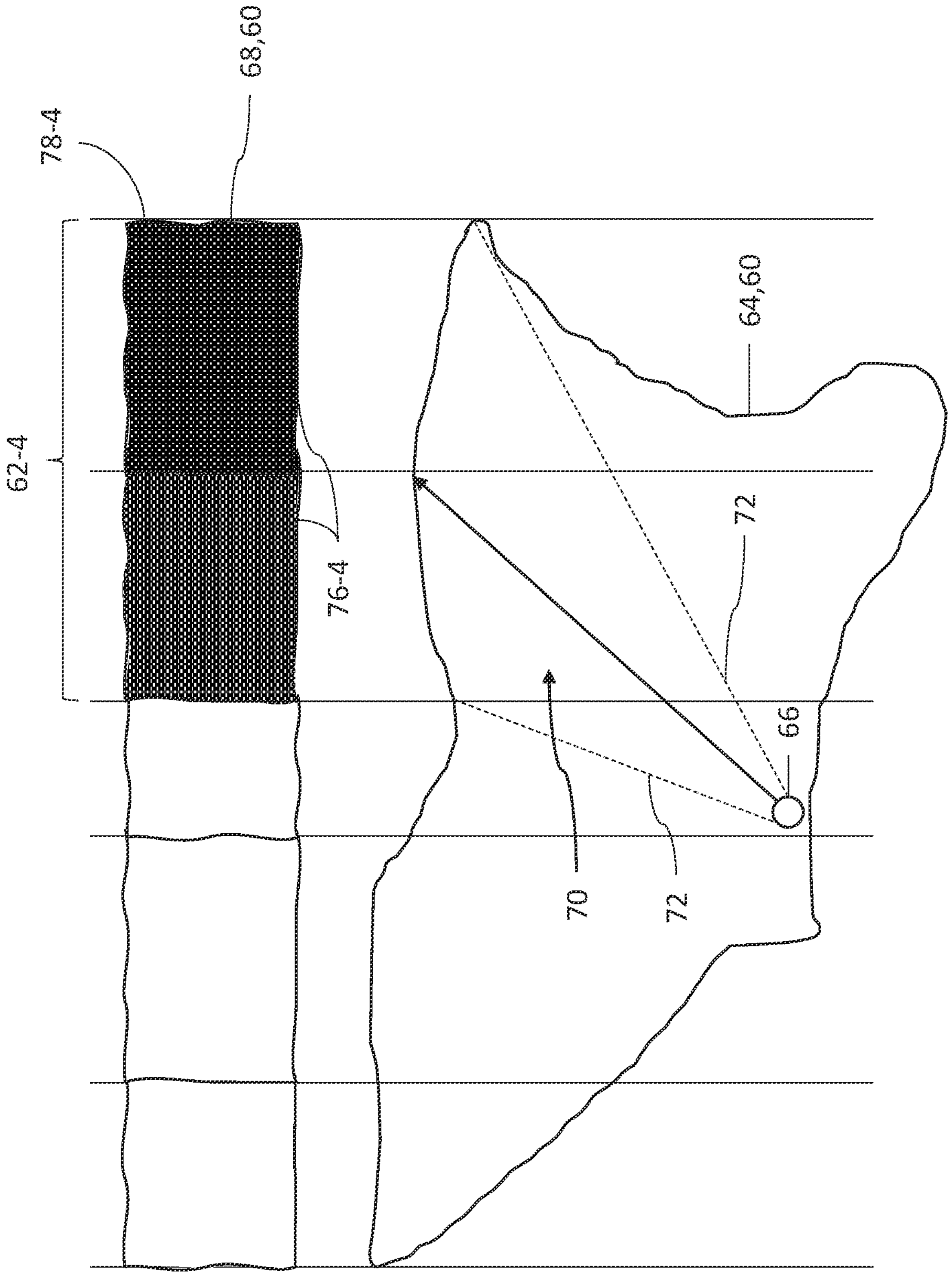
Figure 4E:
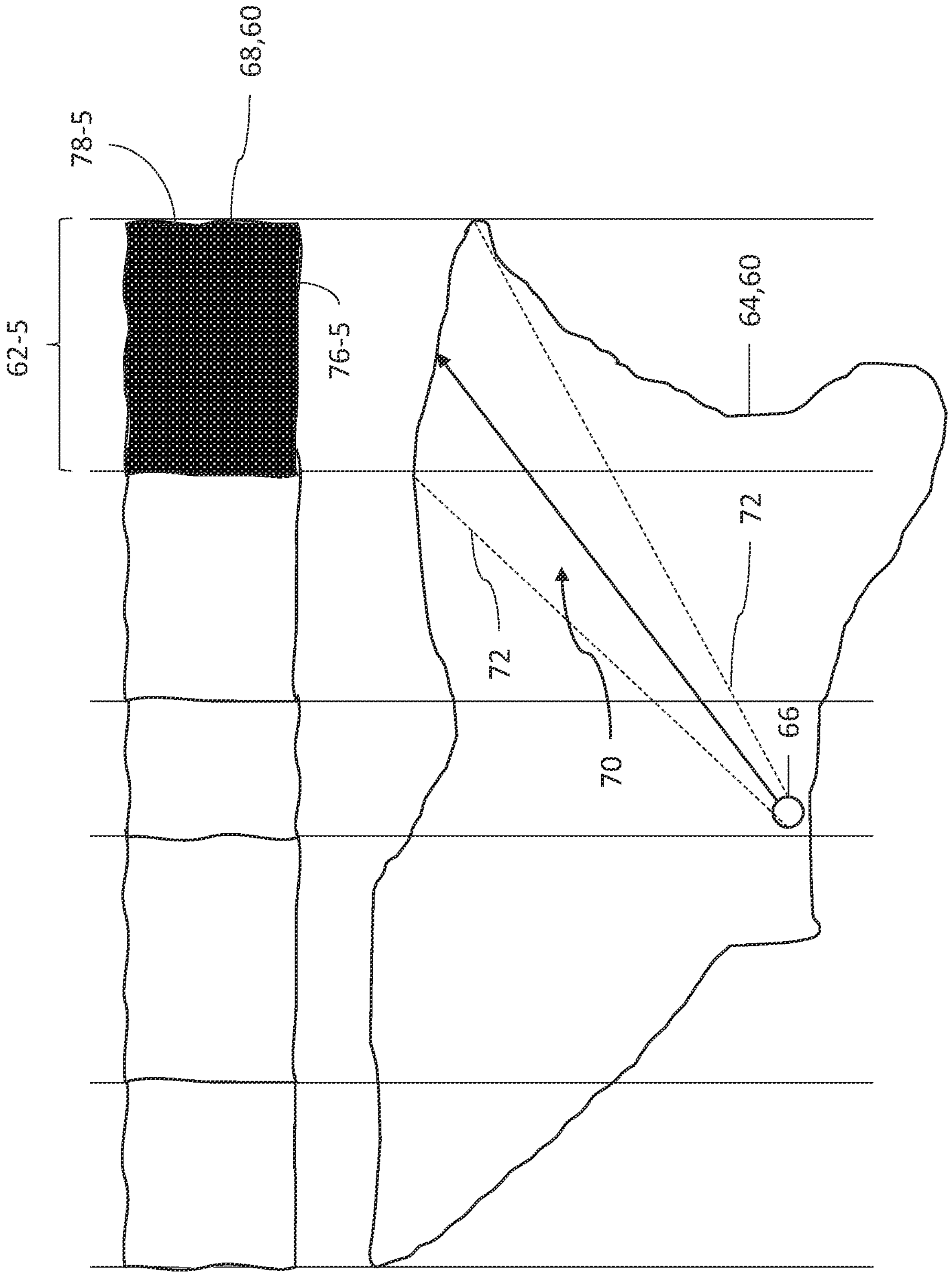

FIGS. 4C-E show the further progression of the cardiac activation wave along the interior wall 68 with shaded regions 76-3, 76-4, 76-5, and corresponding portions 78-3, 78-4, 78-5 of the interior wall 68, being rendered corresponding to LAT ranges 62-3,62-4, 62-5, respectively. It should be noted that FIGS. 4A-E only show the propagation of the cardiac activation wave at discrete points in time. However, the propagation of the cardiac activation wave is generally shown as a smooth transition over the surface of the anatomical map 60 through the cardiac cycle.

In some embodiments, the position of the virtual camera 66 may be moved at a constant rate during the wave propagation. In some embodiments, the position of the virtual camera 66 may be moved at the speed of movement of the wave propagation, i.e., sometime slower and sometimes faster. In some embodiments, the position of the virtual camera 66 may be moved according to a center or leading edge of the cardiac activation wave currently being rendered.

Figure 5:
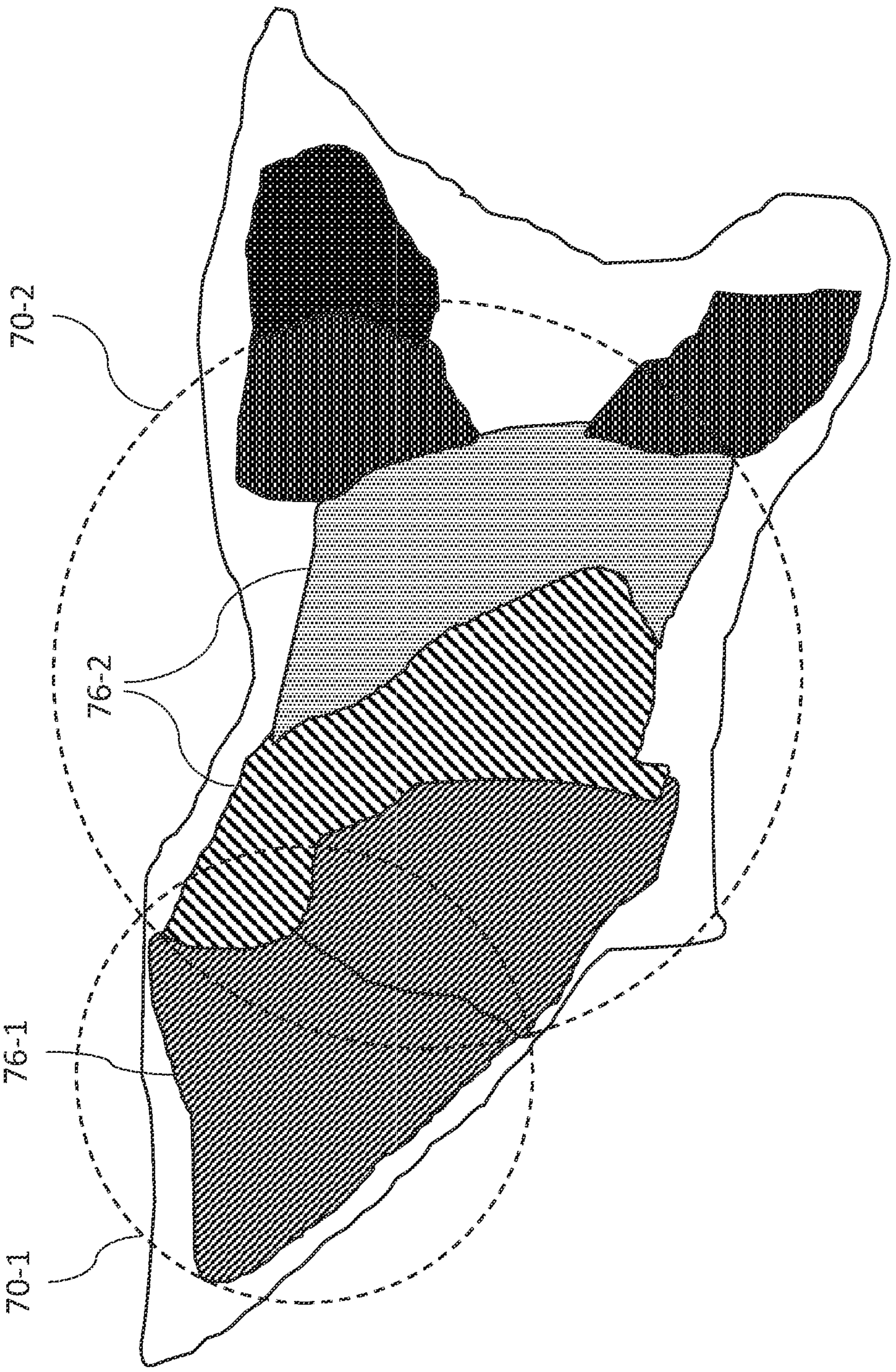
FIG. 5 is a schematic view illustrating adjusting a field of view of a virtual camera in the system of FIG. 1.

Reference is now made to FIG. 5, which is a schematic view illustrating adjusting the field of view of the virtual camera 66 (FIG. 3) in the system 20 of FIG. 1. As the virtual camera 66 is manipulated to follow the propagation of the cardiac activation wave, the field of view of the virtual camera 66 may optionally be adjusted according to the size of the current portion of the wave being propagated. FIG. 5 illustrates that at a first time when the shaded region 76-1 could be rendered as part of the wave propagation at that time, the field of view 70-1 of the virtual camera 66 is adjusted to capture all of the shaded region 76-1, and at a later time when the shaded regions 76-2 could be rendered as part of the wave propagation at that later time, the field of view 70-2 of the virtual camera 66 is adjusted to capture all of the shaded regions 76-2.

Figure 6:
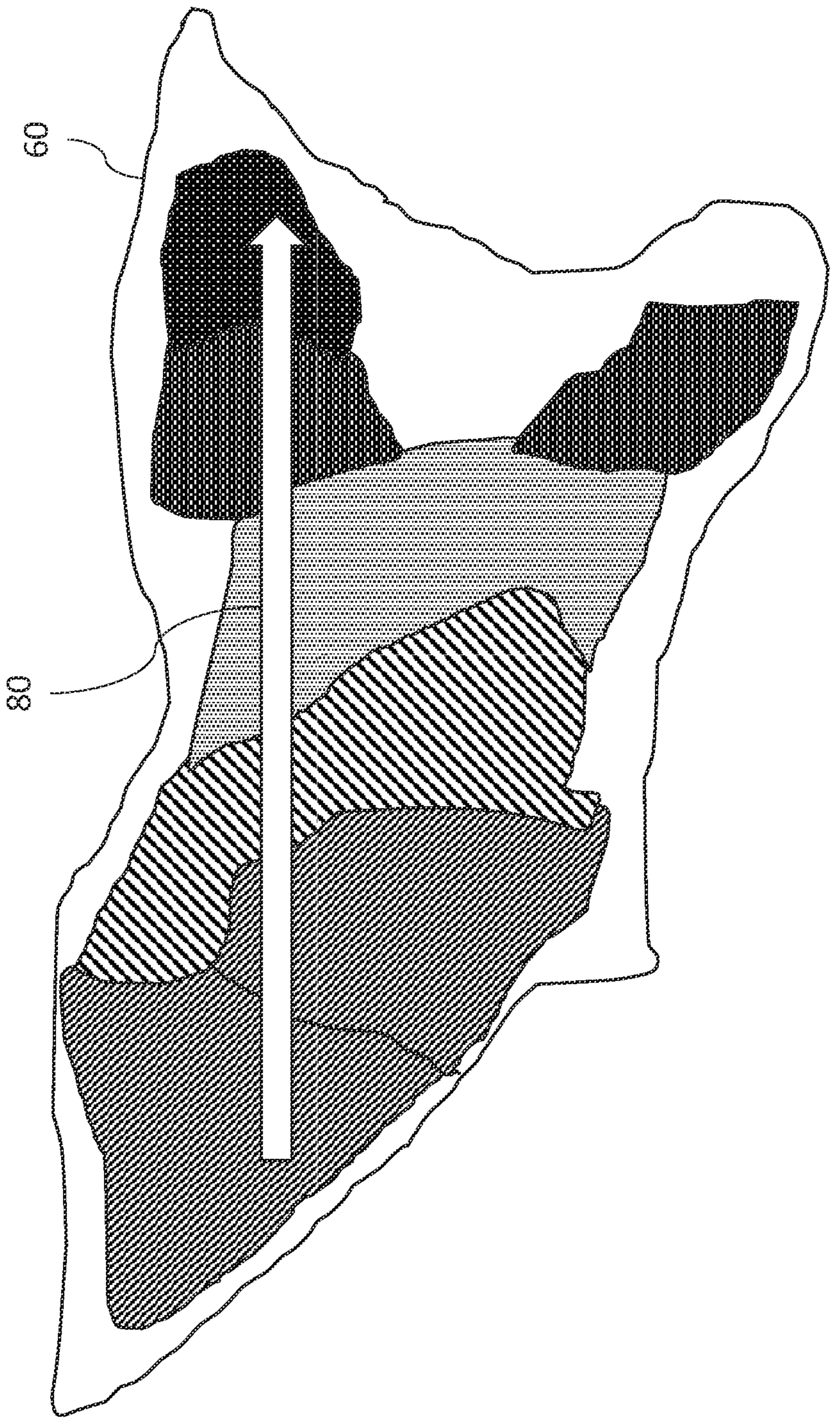
FIG. 6 is a schematic view illustrating a path for a virtual camera to follow for use in the system of FIG. 1.

Reference is now made to FIG. 6, which is a schematic view illustrating a path 80 for the virtual camera 66 (FIG. 3) to follow for use in the system 20 of FIG. 1. The processing circuitry 41 (FIG. 1) may be configured to compute the path 80 for the field of view 70 (FIG. 3) of the virtual camera 66 to follow. The path 80 may be computed based on one or more criteria. For example, the path 80 may be computed to be the longest path of the cardiac activation wave over the anatomical map 60 or the path which traverses the maximum number of LAT values. In some embodiments, the physician 30 (FIG. 1) may draw the path 80 on the anatomical map 60 and then that path 80 is followed by the virtual camera 66 during rendering of the propagation of the cardiac activation wave.

Figure 7:
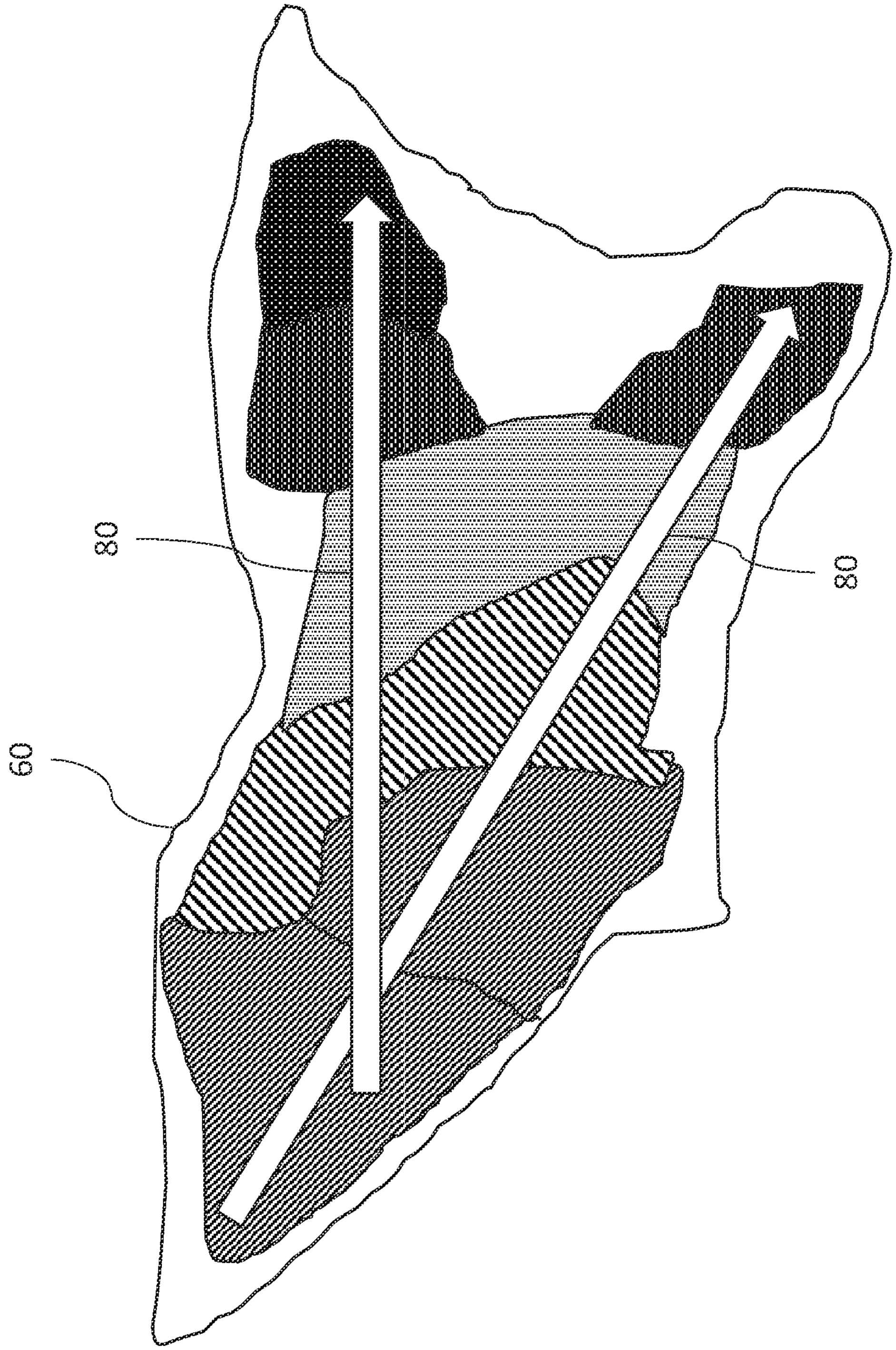
FIG. 7 is a schematic view illustrating possible paths for a virtual camera to follow for use in the system of FIG. 1.

Reference is now made to FIG. 7, which is a schematic view illustrating possible paths 80 for the virtual camera 66 (FIG. 3) to follow for use in the system 20 of FIG. 1. The processing circuitry 41 (FIG. 1) may be configured to compute multiple paths 80 (for example, based on randomly generating paths over the surface of the anatomical map 60) and then select one of the paths 80 based on a variety of criteria. For example, one of the paths 80 may be selected as the longest path of the cardiac activation wave over the anatomical map 60 or the path 80 which traverses the maximum number of LAT values.

In some embodiments, the paths 80 may be rendered to the display 27 (FIG. 1) over the anatomical map 60. The physician 30 (FIG. 1) may then select one of the paths 80 from the anatomical map 60 and then that path 80 is followed by the virtual camera 66 during rendering of the propagation of the cardiac activation wave.

Figure 8:
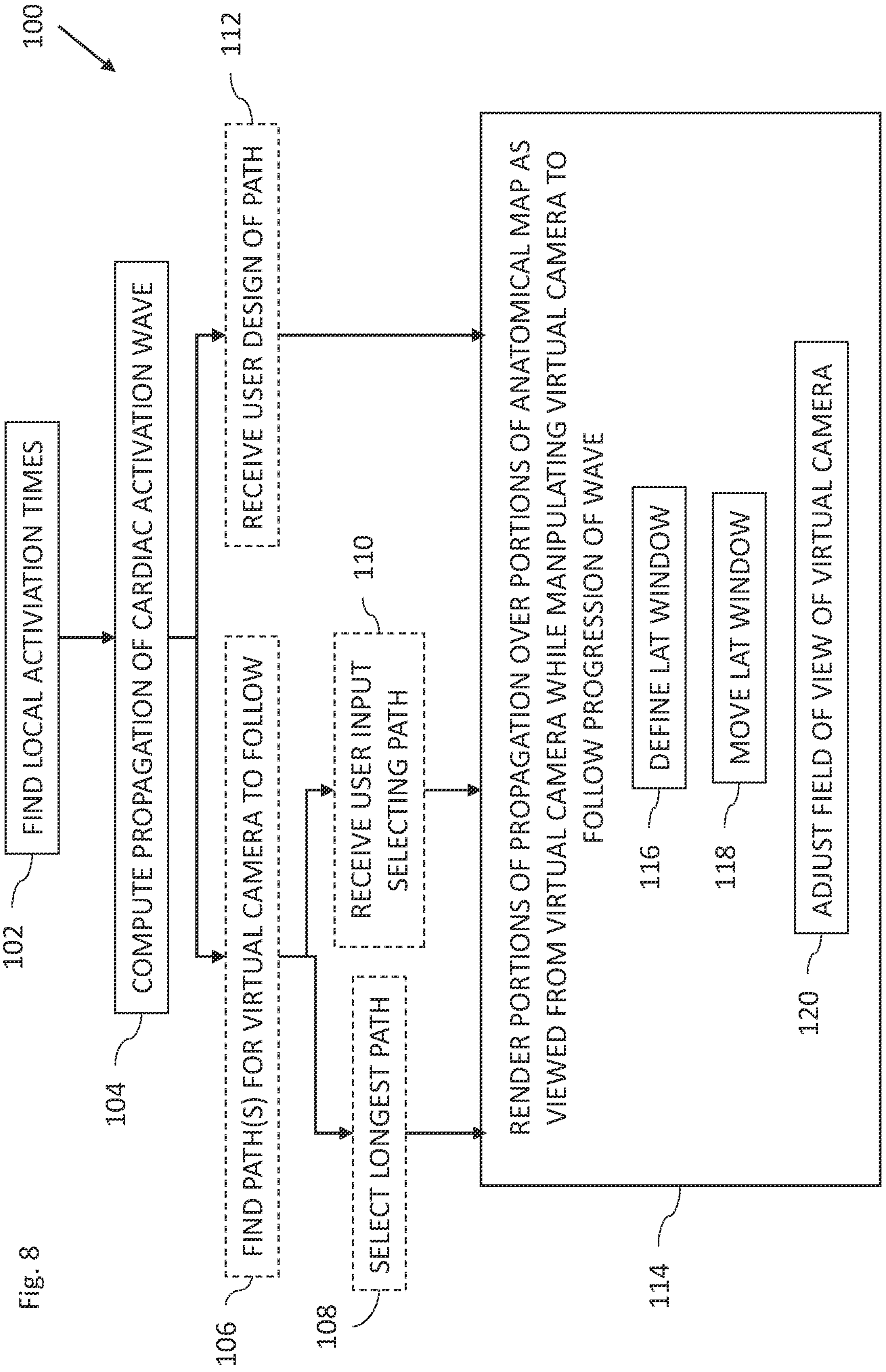
FIG. 8 is a flowchart including steps in a method of operation of the system of FIG. 1.

Reference is now made to FIG. 8, which is a flowchart 100 including steps in a method of operation of the system 20 of FIG. 1.

The processing circuitry 41 is configured to find (block 102) local activation times at corresponding positions on the anatomical map 60 (FIG. 3) responsively to the captured electrical activity, as described above in more detail with reference to FIG. 3. The processing circuitry 41 is configured to compute (block 104) a propagation of a cardiac activation wave over the anatomical map 60 of the chamber of the heart 26 (FIG. 1) from a start time in a cardiac cycle to an end time in the cardiac cycle responsively to the captured electrical activity, as described in more detail with reference to FIG. 3. The propagation of the cardiac activation wave may be computed as the propagation is rendered to the display 27 by activating respective regions of the anatomical map 60 associated with LATs in a current sliding or moving window of LAT values.

In some embodiments, the processing circuitry 41 is configured to find (block 106) one or more paths 80 (FIGS. 6, 7) for the virtual camera 66 (FIG. 3) to follow. The processing circuitry 41 may be configured to select (block 108) one of the paths 80, such as a longest path, as described in more detail with reference to FIG. 7. Additionally, or alternatively, the processing circuitry 41 is configured to receive (block 110) user input selecting one of the paths 80 for the virtual camera 66 to follow. In some embodiments, the processing circuitry 41 is configured to receive user input (block 112), which designs the path 80 (i.e., the path may be designed by the physician 30 on the surface of the anatomical map 60), which the virtual camera 66 will follow.

The processing circuitry 41 is configured to render (block 114) to the display 27 respective portions of the propagation of the cardiac activation wave over respective portions of the anatomical map 60 as viewed from the virtual camera 66 while manipulating the virtual camera 66 to follow progression of the propagation of the cardiac activation wave over the anatomical map 60, as described in more detail with reference to FIGS. 4A-E.

In some embodiments, the virtual camera 66 is disposed inside the anatomical map 60 and the processing circuitry 41 is configured to render to the display 27 the respective portions of the propagation of the cardiac activation wave over the respective portions of the anatomical map 60 as viewed from the virtual camera 66 inside the anatomical map 60 while manipulating the virtual camera 66 to follow progression of the propagation of the cardiac activation wave over the inside surface of the anatomical map 60.

In some embodiments, the processing circuitry 41 is configured to manipulate the virtual camera 66 to follow progression of the propagation of the cardiac activation wave over the anatomical map 60 responsively to respective local activation times at respective corresponding positions on the anatomical map 60. In other words, the LATs found in the step of block 102 have corresponding positions on the anatomical map 60. As the LATs are activated (e.g., highlighted with shading or color) on the anatomical map 60 during propagation of the wave, the virtual camera 66 is manipulated according to the activated LATs. For example, the field of view 70 of the virtual camera 66 is manipulated to follow the center of the activated LAT region, or the leading edge of the activated LAT region.

In some embodiments, the processing circuitry 41 is configured to define (block 116) a local activation time (LAT) window (e.g., a window having a given time width, e.g., 20 ms or 40 ms). The processing circuitry 41 is configured to move (block 118) the LAT window through a time period in the cardiac cycle over respective ranges of the local activation times in the time period. The processing circuitry 41 is configured to render to the display 27 the respective portions of the propagation of the cardiac activation wave over the respective portions of the anatomical map 60 responsively to the respective ranges of the local activation times in the LAT window moving through the time period, and manipulate the virtual camera 66 to follow the progression of the propagation of the cardiac activation wave over the anatomical map 60 responsively to the LAT window moving through the time period, as described above with reference to FIGS. 3 and 4A-F. In other words, as the LAT window is moved, the LATs (i.e., range of LATs) in that window change, and the processing circuitry 41 is configured to render the corresponding portion of the anatomical map 60 (corresponding with the LATs in that window) and the corresponding portion of the propagation of the cardiac activation wave (corresponding with the LATs in that window) and manipulate the virtual camera 66 responsively to the LATs in the window to follow the propagation.

In some embodiments, the processing circuitry 41 is configured to manipulate the virtual camera 66 to follow the progression of the propagation of the cardiac activation wave responsively to the found (and optionally selected) path 80, such as the selected longest path, or the user selected path, or the user designed path, described above with reference to FIGS. 7-8 and the steps of blocks 106-112. By way of example, the field of view 70 of the virtual camera 66 may be manipulated to follow the propagation of the cardiac activation wave along the path 80 at a constant speed by starting at the beginning of the path 80 when the propagation of the cardiac activation wave commences and finishing at the end of the path 80 when the propagation of the cardiac activation wave ends.

In some embodiments, the processing circuitry 41 is configured to manipulate the virtual camera 66 to follow the progression of the propagation of the cardiac activation wave over the anatomical map 60 responsively to the found (and optionally selected) path 80 and respective local activation times at respective ones of the corresponding positions along the found path 80. For example, the field of view 70 of the virtual camera 66 may be manipulated to follow the center of the activated LAT region along the path 80, or the leading edge of the activated LAT region along the path 80. By way of another example, the field of view 70 of the virtual camera 66 may be manipulated to follow the propagation of the cardiac wave along the path 80 based on the speed of the wave, which may be based on the LAT values along the path 80 and the LAT values currently included in the LAT window.

In some embodiments, the processing circuitry 41 is configured to adjust (block 120) the field of view 70 of the virtual camera 66 according to a size (e.g., width of the wave perpendicular to direction of propagation and/or parallel to direction of propagation) of the cardiac activation wave along the found path 80.

As used herein, the terms “about” or “approximately” for any numerical values or ranges indicate a suitable dimensional tolerance that allows the part or collection of components to function for its intended purpose as described herein. More specifically, “about” or “approximately” may refer to the range of values±20% of the recited value, e.g., “about 90%” may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A medical system, coupled with a catheter to be inserted into a chamber of a heart, the catheter including electrodes, the medical system comprising:

processing circuitry configured to:

receive electrical activity of heart tissue captured by electrodes of the catheter;

compute a propagation of a cardiac activation wave over a three-dimensional anatomical map of the chamber of the heart from a start time in a cardiac cycle to an end time in the cardiac cycle responsively to the received electrical activity;

render to a display respective portions of the propagation of the cardiac activation wave over respective portions of the three-dimensional anatomical map as viewed from a virtual camera, while manipulating the virtual camera to follow progression of the propagation of the cardiac activation wave over the anatomical map;

find local activation times at corresponding positions on the three-dimensional anatomical map responsively to the received electrical activity;

define a local activation time (LAT) window having a given time width;

move the LAT window through a time period in the cardiac cycle over respective ranges of the local activation times in the time period; and repeatedly render to a display the respective portions of the propagation of the cardiac activation wave over the respective portions of the three-dimensional anatomical map as viewed from the virtual camera while automatically manipulating the virtual camera to follow progression of the propagation of the cardiac activation wave over the three-dimensional anatomical map responsively to respective ones of the local activation times at respective ones of the corresponding positions and responsively to the respective ranges of the local activation times in the LAT window moving through the time period, wherein the processing circuitry is further configured to:

find a path for the virtual camera to follow;

manipulate the virtual camera to follow the progression of the propagation of the cardiac activation wave responsively to the found path; and adjust a field of view of the virtual camera according to a size of the cardiac activation wave along the found path.

2. The system according to claim 1, wherein: the virtual camera is disposed inside the three-dimensional anatomical map; and the processing circuitry is configured to render to the display the respective portions of the propagation of the cardiac activation wave over the respective portions of the three-dimensional anatomical map as viewed from the virtual camera inside the three-dimensional anatomical map while manipulating the virtual camera to follow progression of the propagation of the cardiac activation wave over the inside of the three-dimensional anatomical map.

3. The system according to claim 1, wherein the processing circuitry is configured to:

find local activation times at corresponding positions on the three-dimensional anatomical map responsively to the received electrical activity; and render to the display the respective portions of the propagation of the cardiac activation wave over the respective portions of the three-dimensional anatomical map as viewed from the virtual camera while manipulating the virtual camera to follow the progression of the propagation of the cardiac activation wave over the three-dimensional anatomical map responsively to the found path and respective ones of the local activation times at respective ones of the corresponding positions along the found path.

4. The system according to claim 1, wherein the processing circuitry is configured to receive user input, which designs the path.

5. The system according to claim 1, wherein the processing circuitry is configured to find a plurality of paths for the virtual camera to follow.

6. The system according to claim 5, wherein the processing circuitry is configured to: select a longest one of the paths; and manipulate the virtual camera to follow the progression of the propagation of the cardiac activation wave responsively to the longest one of the paths.

7. The system according to claim 5, wherein the processing circuitry is configured to receive user input selecting one of the paths for the virtual camera to follow.

8. A medical method, comprising:

computing a propagation of a cardiac activation wave over a three-dimensional anatomical map of a chamber of a heart from a start time in a cardiac cycle to an end time in the cardiac cycle responsively to electrical activity of tissue of a chamber of a heart captured over time by electrodes of a catheter inserted into the chamber;

rendering to a display respective portions of the propagation of the cardiac activation wave over respective portions of the three-dimensional anatomical map as viewed from a virtual camera while manipulating the virtual camera to follow progression of the propagation of the cardiac activation wave over the three-dimensional anatomical map;

finding local activation times at corresponding positions on the three-dimensional anatomical map responsively to the captured electrical activity;

defining a local activation time (LAT) window having a given time width; and moving the LAT window through a time period in the cardiac cycle over respective ranges of the local activation times in the time period, wherein the rendering includes repeatedly rendering to the display the respective portions of the propagation of the cardiac activation wave over the respective portions of the three-dimensional anatomical map as viewed from the virtual camera while automatically manipulating the virtual camera to follow progression of the propagation of the cardiac activation wave over the three-dimensional anatomical map at a predetermined rate, responsively to respective ones of the local activation times at respective ones of the corresponding positions and responsively to the respective ranges of the local activation times in the LAT window moving through the time period, wherein the method further comprises:

finding a path for the virtual camera to follow, wherein the manipulating includes manipulating the virtual camera to follow the progression of the propagation of the cardiac activation wave responsively to the found path, and adjusting a field of view of the virtual camera according to a size of the cardiac activation wave along the found path.

9. The method according to claim 8, wherein:

the virtual camera is disposed inside the three-dimensional anatomical map; and the rendering includes rendering to the display the respective portions of the propagation of the cardiac activation wave over the respective portions of the three-dimensional anatomical map as viewed from the virtual camera inside the three-dimensional anatomical map while manipulating the virtual camera to follow progression of the propagation of the cardiac activation wave over the inside of the three-dimensional anatomical map.

10. The method according to claim 8, wherein:

the finding includes finding local activation times at corresponding positions on the three-dimensional anatomical map responsively to the captured electrical activity; and the rendering includes rendering to the display the respective portions of the propagation of the cardiac activation wave over the respective portions of the three-dimensional anatomical map as viewed from the virtual camera while manipulating the virtual camera to follow the progression of the propagation of the cardiac activation wave over the three-dimensional anatomical map responsively to the found path and respective ones of the local activation times at respective ones of the corresponding positions along the found path.

11. The method according to claim 8, further comprising receiving user input, which designs the path.

12. The method according to claim 8, further comprising finding a plurality of paths for the virtual camera to follow.

13. The method according to claim 12, further comprising selecting a longest one of the paths, and wherein the manipulating includes manipulating the virtual camera to follow the progression of the propagation of the cardiac activation wave responsively to the longest one of the paths.

14. The method according to claim 12, further comprising receiving user input selecting one of the paths for the virtual camera to follow.

* * * * *